(12) United States Patent
Simhambhatla et al.

(10) Patent No.: US 6,428,506 B1
(45) Date of Patent: Aug. 6, 2002

(54) MEDICAL DEVICE FORMED OF ULTRAHIGH MOLECULAR WEIGHT POLYETHYLENE

(75) Inventors: Murthy V. Simhambhatla, San Jose; Robert D. Ainsworth, Scotts Valley; Robert P. Saltman, Redwood City, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/470,056

(22) Filed: Dec. 22, 1999

(51) Int. Cl.$^7$ .................... A61M 29/00; B29D 22/00
(52) U.S. Cl. ................... 604/96.01; 428/36.9
(58) Field of Search .............. 604/96.01, 103.06, 604/103.08, 103.13; 428/35.7, 36.9, 36.91, 36.92

(56) References Cited

U.S. PATENT DOCUMENTS

| | | | |
|---|---|---|---|
| 4,279,245 A | 7/1981 | Takagi et al. | 128/4 |
| 4,482,516 A | 11/1984 | Bowman et al. | 264/127 |
| 4,655,769 A | 4/1987 | Zachariades | 623/1 |
| 4,668,557 A | 5/1987 | Lakes | 428/131 |
| 4,833,172 A | 5/1989 | Schwarz et al. | 521/62 |
| 5,335,675 A | 8/1994 | Wheeler et al. | 128/842 |
| 5,499,973 A | 3/1996 | Saab | 604/96 |
| 5,569,196 A | 10/1996 | Muni et al. | 604/96 |
| 5,752,934 A | 5/1998 | Campbell et al. | 604/96 |
| 5,753,358 A | 5/1998 | Korleski | 428/308.4 |
| 5,782,903 A | * 7/1998 | Wiktor | 623/1 |
| 5,788,626 A | 8/1998 | Thompson | 600/36 |
| 6,165,166 A | 12/2000 | Samuelson et al. | 604/524 |

FOREIGN PATENT DOCUMENTS

| | | |
|---|---|---|
| EP | 0 253 513 | 1/1988 |
| EP | 0 267 719 | 5/1988 |
| EP | 0 313 263 | 4/1989 |
| EP | 0 376 503 | 12/1989 |
| WO | WO91/01210 | 2/1991 |

OTHER PUBLICATIONS

Harvey L. Stein, Ultrahigh Molecular Weight Polyethylenes (UHMWPE), Engineered Materials Handbook—vol. 2: Engineering Plastics, 167–171.

Caddock et al. "Microporous materials with negative Poisson's ratios: I. Microstructure and mechanical properties", Journal of Physics D: Applied Physics, 22(12):1877–1882 (1989).

* cited by examiner

Primary Examiner—Sharon Kennedy
(74) Attorney, Agent, or Firm—Fulwider Patton Lee & Utecht, LLP

(57) ABSTRACT

Medical devices such as catheter balloons, stent covers and vascular grafts formed of ultrahigh molecular weight polyethylene. The devices are formed from polyethylene that has been processed so that it is microporous and has an oriented node and fibril structure. The balloons expand compliantly at low strains and are substantially less compliant at higher strains. The invention also comprises methods for making such balloons, including the steps of compacting a polyethylene powder and deforming it to impart the oriented structure.

16 Claims, 2 Drawing Sheets

MEDICAL DEVICE FORMED OF ULTRAHIGH MOLECULAR WEIGHT POLYETHYLENE

BACKGROUND OF THE INVENTION

This invention generally relates to medical devices, and particularly to balloon catheters, stent covers, and vascular grafts.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of an dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion. The framework of the stent may still allow migration and proliferation of the smooth muscle cells, while the stent itself can be thrombogenic. To address these problems, stent covers on a surface of the stent have been used. Stent covers have been used in, for example, the treatment of pseudo-aneurysms and perforated arteries, and to prevent prolapse of plaque. Similarly, vascular grafts comprising cylinders made from tissue or synthetic materials such as DACRON may be implanted in vessels to strengthen or repair the vessel, or used in an anastomosis procedure to connect vessels segments together.

In the design of catheter balloons, balloon characteristics such as strength, flexibility and compliance must be tailored to provide optimal performance for a particular application. Angioplasty balloons preferably have high strength for inflation at relatively high pressure, and high flexibility and softness for improved ability to track the tortuous anatomy and cross lesions. The balloon compliance is chosen so that the balloon will have a desired amount of expansion during inflation. Compliant balloons, for example balloons made from materials such as polyethylene, exhibit substantial stretching upon the application of tensile force. Noncompliant balloons, for example balloons made from materials such as PET, exhibit relatively little stretching during inflation, and therefore provide controlled radial growth in response to an increase in inflation pressure within the working pressure range.

For many applications, intravascular catheter balloons should be substantially noncompliant once expanded to a working diameter. Further, catheter balloons should also be formed from relatively strong materials in order to withstand the pressures necessary for various procedures without failing. Typically, such characteristics require the use of a material that does not stretch, which consequently necessitates that the balloon material be folded around the catheter shaft prior to inflation. However, it can be desirable to employ balloons that are not folded prior to inflation, but which are instead expanded to the working diameter from a generally cylindrical shape having a nominal diameter that conforms to the catheter shaft. Such designs may be used for formed-in-place angioplasty balloons and stent delivery balloons. Prior art formed-in-place balloons have suffered from problems such as insufficient strength, poor control over expansion, and significantly complicated processing during catheter manufacturing.

It would be a significant advance to provide a catheter balloon, and other expandable members such as stent covers, and vascular grafts, with improved processing and expansion characteristics.

SUMMARY OF THE INVENTION

This invention is directed to medical devices having at least a component formed of ultrahigh molecular weight polyethylene (herein after "UHMW polyethylene"). In a presently preferred embodiment, the UHMW polyethylene is microporous with a node and fibril microstructure comprising nodes interconnected by fibrils. One embodiment of the invention comprises a balloon for an intraluminal catheter, formed at least in part of the UHMW polyethylene. In another embodiment of the invention, a stent delivery system comprising a balloon catheter and a stent mounted on the balloon has a component, such as the catheter balloon or a stent cover, which is formed at least in part of the UHMW polyethylene. Another embodiment of the invention comprises a vascular graft formed at least in part of the UHMW polyethylene. Although discussed below primarily in terms of a balloon catheter having a balloon formed of UHMW polyethylene, the invention should be understood to include other medical devices such as stent covers and vascular grafts formed of UHMW polyethylene.

The UHMW polyethylene has a molecular weight which is higher than the molecular weight of high molecular weight polyethylenes, and which is about 2 million to about 10 million grams/mole, preferably about 3 million to about 6 million grams/mole. Unlike high molecular weight polyethylenes, which generally have a molecular weight of about 400,000 to about 600,000 grams/mole, the UHMW polyethylene is typically not melt processable. Balloons formed from this material exhibit compliant expansion at relatively low strains and exhibit substantially less compliance at higher strains.

The node and fibril structure of the UHMW polyethylene causes it to exhibit essentially compressible deformation at relatively small strains, with a low Young's modulus. At high strains, the UHMW polyethylene balloons of the invention preferably exhibit low compliance due to rearrangement in the microstructure. Embodiments of the invention suited to intravascular applications preferably exhibit compliant radial expansion of about 100% to about 400% of the uninflated diameter, at pressures up to about 6 to about 8 atm. Once expanded, the balloons exhibit relatively low compliance at pressures above 8 atm and can have a burst pressure of at least about 18 atm. For stent delivery applications, the polyethylene preferably has a foamlike compressible state at low strains so that the stent can be crimped onto the balloon with good retention.

Balloon catheters of the invention generally comprise an elongated shaft with at least one lumen and a UHMW polyethylene balloon on a distal shaft section with an interior in fluid communication with the shaft lumen. The balloon catheters of the invention may be configured for a variety of uses, such as angioplasty or stent delivery. A stent delivery catheter employs a balloon having the characteristics of the invention to deploy the stent. Preferably, the oriented polyethylene exhibits a foam-like compressible state at low strains, facilitating crimping of the stent onto the balloon with improved stent retention. In accordance with the invention, the stent may be provided with a stent cover generally comprising a tubular sheath formed of the UHMW polyethylene and configured to be disposed on an outer and/or inner surface of the stent and implanted with the stent in the patient's vessel.

Vascular grafts of the invention generally comprise a tubular body formed of the UHMW polyethylene. The vascular graft is configured to be implanted in a patient, and may be used for a variety of procedures including anastomosis, bypass surgery, and aneurysm repair.

The invention also comprises methods of forming a medical device component such as a balloon, stent cover or vascular graft, from microporous polyethylene having an oriented node and fibril structure. Generally, the method comprises the steps of compacting ultrahigh molecular weight polyethylene powder, deforming the compacted polyethylene to render the polyethylene microporous and to impart an oriented node and fibril structure to the polyethylene, and forming the medical device component from the polyethylene. Optionally, the powder can be sintered prior to deformation. Also optionally, the oriented polyethylene can be heat set. Preferably, a tubular medical device component such as a balloon may be formed by wrapping a sheet of the oriented polyethylene around a mandrel to form a tube and then heat fusing the polyethylene layers together, or by directly producing an oriented tubular member.

The medical devices such as catheter balloons, stent covers, and vascular grafts of the invention have improved performance due to the UHMW polyethylene which is microporous, biocompatible, and biostable, and which has excellent mechanical properties. Further, UHMW polyethylene is compatible with electron-beam (i.e., e-beam) sterilization, unlike expanded polytetrafluoroethylene (i.e., ePTFE), which degrades when exposed to e-beams. As a result, medical devices such as balloons of this invention can be expanded compliantly to their working diameter but exhibit substantially less compliance at greater pressures, providing control over expansion even at pressures suitable for conventional intravascular procedures such as angioplasty or stent delivery. Further, the formed-in-place balloons of the invention have sufficient strength to improve the safety of conventional intravascular procedures. UHMW polyethylene also facilitates device manufacture, because the processing temperatures for polyethylene are relatively low, and the polyethylene can be heat bonded or attached with adhesives to other device components.

These and other advantages of the invention will become more apparent from the following detailed description when taken in conjunction with the accompanying exemplary drawings.

DETAILED DESCRIPTION OF THE INVENTION

Figure 1:
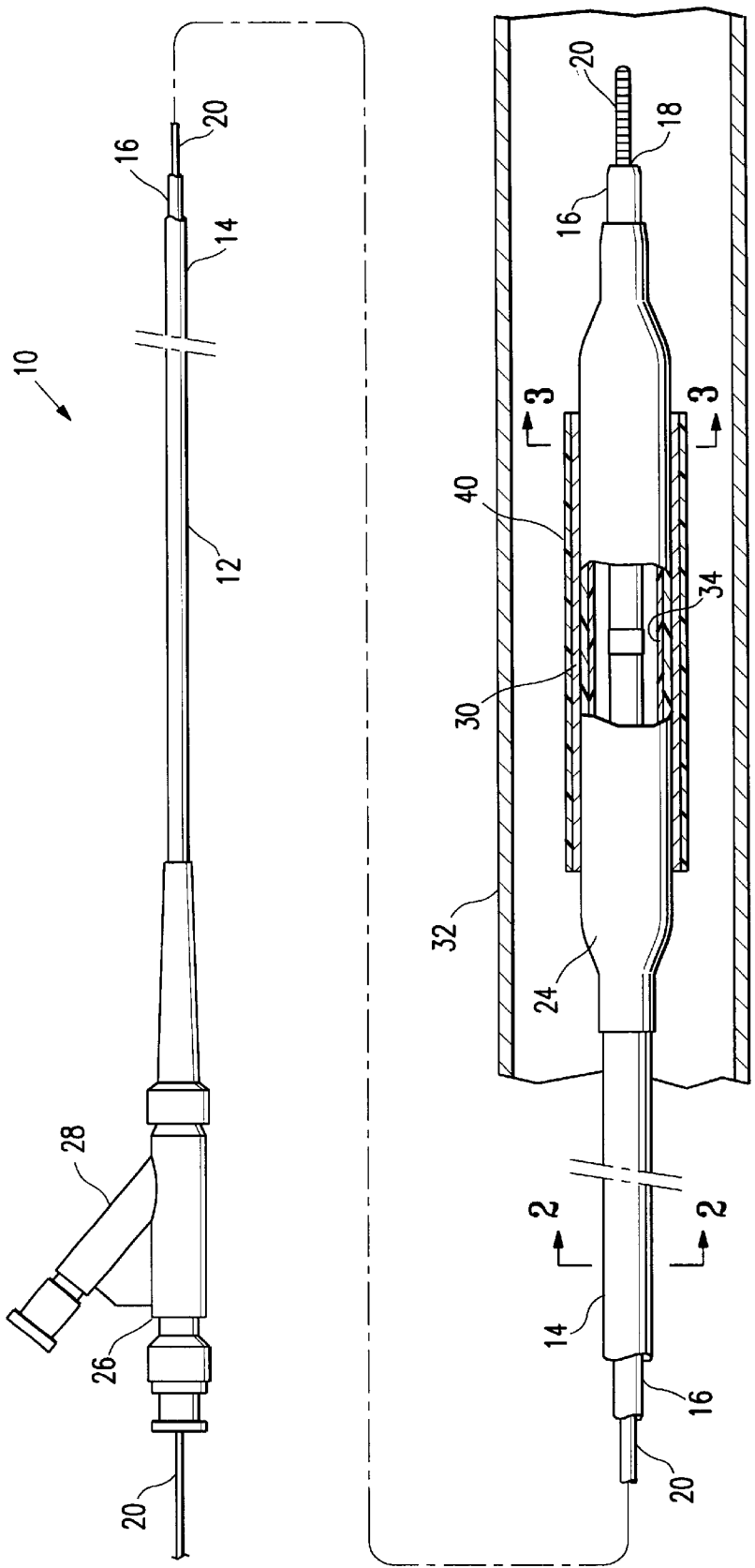
FIG. 1 is an elevational view, partially in section, of a balloon catheter for delivering a stent that embodies features of the invention.
Figure 3:
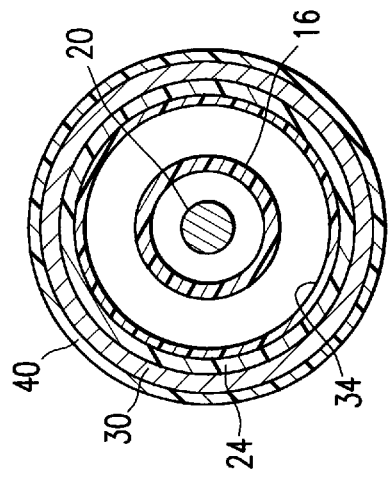
FIG. 3 is a transverse cross-section of the catheter shown in FIG. 1 taken at line 3—3, showing the stent disposed over the inflatable balloon.
Figure 2:
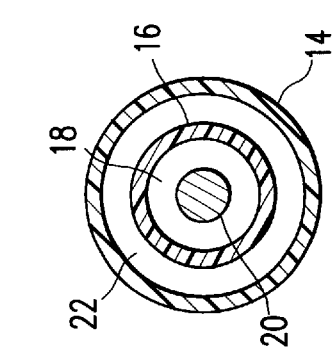
FIG. 2 is a transverse cross-section of the catheter shown in FIG. 1 taken at line 2—2.
Figure 4:
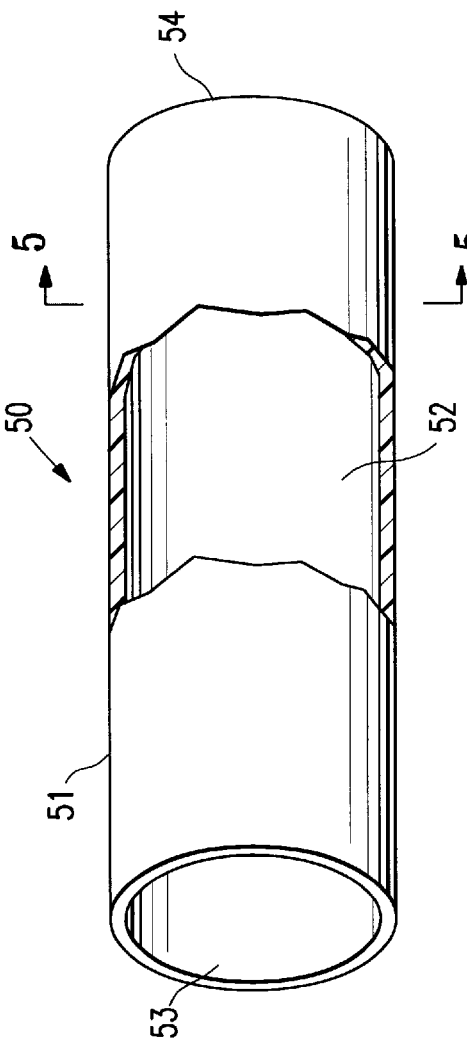
FIG. 4 is an elevational view, partially in section, of a vascular graft or stent cover which embodies features of the invention.

FIGS. 1–3 illustrate an over-the-wire type stent delivery balloon catheter 10 embodying features of the invention. Catheter 10 generally comprises an elongated catheter shaft 12 having an outer tubular member 14 and an inner tubular member 16. Inner tubular member 14 defines a guidewire lumen 18 adapted to slidingly receive a guidewire 20. The coaxial relationship between outer tubular member 14 and inner tubular member 16 defines annular inflation lumen 22. An inflatable balloon 24 disposed on a distal section of catheter shaft 12 having a proximal end sealingly secured to the distal end of outer tubular member 14 and a distal end sealingly secured to the distal end of inner tubular member 16 so that its interior is in fluid communication with inflation lumen 22. An adapter 26 at the proximal end of catheter shaft 12 is configured to direct inflation fluid through arm 28 into inflation lumen 22.

In the embodiment illustrated in FIG. 1, an expandable stent 30 is mounted on balloon 24. The distal end of catheter may be advanced to a desired region of a patient's lumen 32 in a conventional manner and balloon 24 may be inflated to expand stent 30, seating it in the lumen.

In the embodiment illustrated in FIG. 1, the balloon 24 has a layer 34 formed from an elastomeric material. In the preferred embodiment illustrated, elastomeric layer 34 is on the interior of balloon 24, although in other embodiments it may be on the exterior or the balloon 24. Elastomeric layer 34 expands elastically to facilitate deflation of the balloon 24 to its preinflation diameter and shape, and can also limit or prevent leakage of inflation fluid through the microporous polyethylene.

Balloon 24 is formed at least in part of a UHMW polyethylene. Preferably, the UHMW polyethylene has a molecular weight of about 3 million to about 6 million. Suitable UHMW polyethylenes are available from Hoechst Celanese, and described in Ultrahigh Molecular Weight Polyethylenes (UHMWPE), Engineered Materials Handbook, Vol. 2: Engineering Plastics, H. L. Stein, and WO 91/01210, incorporated by reference herein in its entirety. Presently preferred UHMW polyethylenes are classified by molecular weight determinations detailed in ASTM (American Society for Testing and Methods) D 1601 and D 4020. In a presently preferred embodiment, the UHMW polyethylene is processed so that it is microporous and exhibits an oriented structure comprising nodes interconnected by fibrils. The microporous UHMW polyethylene with an oriented node and fibril microstructure has a porosity of about 20% to about 90%, and an internodal distance, also expressed as fibril length, of about 5 μm to about 200 μm. Examples of microporous UHMW polyethylenes, having a node and fibril microstructure and a suitably high orientation, are described in WO 91/01210, incorporated by reference herein in its entirety. As described in WO 91/01210, such UHMW polyethylene materials may exhibit a negative Poisson ratio. Balloons formed from this material exhibit compliant expansion at relatively low strains and exhibit substantially less compliance at higher strains. For example, in a presently preferred embodiment, balloon 24 expands compliantly by about 100% to about 400% of the uninflated diameter at pressures of about 6 to about 8 atm. Once expanded, the balloon 24 is relatively noncompliant at pressures greater than about 8 atm, up to the burst pressure of the balloon which preferably is at least about 18 atm.

In the embodiment illustrated in FIG. 1, a stent cover 40 formed of the UHMW polyethylene is disposed on an outer surface of the stent 30. As discussed above, the UHMW polyethylene forming the stent cover 40 can be processed to be microporous with a node and fibril microstructure. Stent cover 40 is secured to the surface of the stent 30 before the stent is introduced into the patient's vasculature, and expanded, together with the stent, to implant the stent and stent cover thereon in the vessel lumen. Stent cover 40 secured to the stent has a generally tubular structure conforming to a surface of the stent. In the presently preferred embodiment illustrated in FIG. 1, the stent cover 40 extends the length of the stent 30. However, in alternative embodiments the stent cover may have a length longer than or shorter than a length of the stent. The stent cover 40 length may be selected to fit a variety of conventionally sized stents, with a typical diameter of about 2 mm to about 10 mm. The stent cover 40 wall thickness is typically about 20 μm to about 400 μm, preferably about 40 μm to about 100 μm. The stent cover 40 provides a biocompatible, biostable surface on the stent, which reduces plaque prolapse through the stent struts. A stent cover may be provided on an inner surface of the stent (not shown).

Figure 5:
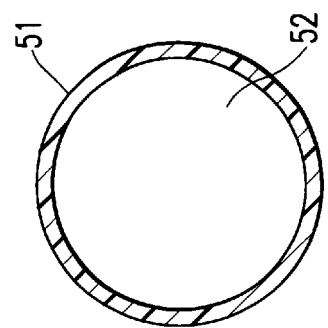
FIG. 5 is a transverse cross-section of the graft or cover shown in FIG. 4, taken along lines 5—5.

In another embodiment of the invention illustrated in FIG. 5, vascular graft 50 comprises a tubular body 51 having a lumen 52 therein, formed of an UHMW polyethylene. Ports 53,54 are at either end of the graft 50. As discussed above the UHMW polyethylene can be processed to be microporous with a node and fibril microstructure. The graft is configured for being implanted in the patient, and it may be expanded into place within a vessel or surgically attached to a free end of a vessel. The graft 50 length is generally about 4 to about 80 mm, and more specifically about 10 to about 50 mm, depending on the application, and wall thickness is typically about 40 μm to about 2000 μm, preferably about 100 μm to about 1000 μm. The diameter is generally about 1 to about 35 mm, preferably about 3 to about 12 mm, depending on the application.

A process of forming the microporous node and fibril structure of the UHMW polyethylene generally comprises compacting polyethylene powder and then deforming it to impart the node and fibril structure. The step of compacting the polyethylene powder can by any suitable means including the presently preferred embodiments of applying pressure, with or without additional heat, or forming a slurry with a lubricating medium and then extruding the slurry through a die. The lubricating medium should be evaporated from the slurry after extrusion. When applying pressure and heating the polymer powder, the polyethylene may be heated to a temperature at or above its softening point, but below its melting point, to sinter the material. For example, preferred UHMW polyethylene blends have a sintering temperature of about 160° C. The size and shape of the polyethylene particles can be chosen to influence the node and fibril structure and optimize the properties of the resulting material. For example, the shape of the particles tends to be reflected in the shape of the nodes.

The particle size is generally about 0.1 μm to about 250 μm, preferably 0.1 μm to about 40 μm.

The compacted powder is then deformed to impart the oriented node and fibril structure. Typically, the polyethylene is deformed by stretching or by extrusion through a die. The deformation step may be performed either at ambient or elevated temperatures. In a preferred embodiment, sintered polyethylene is ram extruded at ambient temperature to form a sheet of material, which is then rapidly stretched, axially or bi-axially, to orient the structure. Optionally, the stretched material can be heat set. The processing of the polyethylene also renders it microporous, and the amount of stretch experienced by the material controls the distance between the nodes and the corresponding fibril length.

One presently preferred method of forming the UHMW polyethylene generally comprises preparing a homogeneous paste of UHMW polyethylene in a low boiling mineral oil. The paste is then compacted into a billet by applying pressure and optionally applying heat. The billet is then loaded into a ram extruder and a tube or film is extruded. The extrusion may be done at room temperature, or the temperature may be elevated. The oil is then evaporated from the UHMW polyethylene by heating the film to a temperature not exceeding the melting point of the UHMW polyethylene. The film or tube is then uniaxially or bi-axially oriented to produce the oriented node and fibril structure. The oriented tube may then optionally be heat set at temperatures just above the melting point of UHMW polyethylene, which has a crystalline melting point of about 130–140° C.

Another presently preferred process comprises compacting UHMW ethylene particles into a billet at temperatures below the melting point. Preferably, this step would be done at about 100–120° C. Preferably, the pressure applied is about 0.01 GPa to about 0.08 GPa. The billet is sintered at temperatures above the crystalline melting point without applying any pressure. This step is completed at a preferred temperature of about 130–160° C. The sintered billet is extruded through a film or annular die in a ram extruder. The UHMW polyethylene is then optionally oriented and heat set as described above.

Generally, the balloons of the invention are formed from the sheet of stretched material. The material is wrapped around a mandrel to form a tube and then heated to fuse the wrapped material together. The resulting parison may be secured to the conventional catheter components by laser bonding or plasma treatment followed by adhesive bonding.

The dimensions of catheter 10 are determined largely by the size of the guidewires to be employed and the size of the artery or other body lumen through which the catheter must pass or the size of the stent being delivered. Typically, the outer tubular member 14 has an outer diameter of about 0.02 to about 0.04 inch (0.05 to 0.10 cm), usually about 0.037 inch (0.094 cm), an inner diameter of about 0.015 to about 0.035 inch (0.038 to 0.089 cm), usually about 0.03 inch (0.076 cm). The wall thickness of the outer tubular member 14 can vary from about 0.002 to about 0.008 inch (0.0051 to 0.0201 cm), typically about 0.003 inch (0.0076 cm). The inner tubular member 15 typically has an outer diameter of about 0.012 to about 0.016 inch (0.030 to 0.041 cm), usually about 0.014 inch (0.036 cm). The overall length of the catheter 10 may range from about 100 to about 150 cm, and is typically about 135 cm. Preferably, balloon 24 may have a length about 0.5 cm to about 4 cm and typically about 2 cm with an inflated working diameter of about 1 to about 8 mm. Inner tubular member 16 and outer tubular member 14 can be formed by conventional techniques, for example by extruding, from materials already found useful in intravascular catheters such a polyethylene, polyvinyl chloride, polyesters, polyamides, polyimides and composite materials. The various components may be joined by heat bonding or use of adhesives.

While the present invention is described herein in terms of certain preferred embodiments, those skilled in the art will recognize that various modifications and improvements may be made to the invention without departing from the scope thereof. For example, in the embodiment illustrated in FIG. 1, the catheter is a stent delivery catheter. However, one of skill in the art will readily recognize that the balloons of this invention may also be used with other types of intravascular catheters, such as over-the-wire and rapid exchange dilatation catheters. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. A balloon for an intraluminal catheter, wherein the balloon comprises ultrahigh molecular weight polyethylene.

2. The balloon of claim 1, wherein the polyethylene is a microporous polyethylene having a node and fibril microstructure comprising nodes interconnected by fibrils.

3. The balloon of claim 2, wherein the polyethylene has an internodal distance of about 5 $\mu$m to about 200 $\mu$m.

4. The balloon of claim 1, wherein the polyethylene has a molecular weight of about 3 million to about 6 million.

5. The balloon of claim 1, wherein the polyethylene is formed of particles having a size of about 0.1 $\mu$m to about 250 $\mu$m.

6. The balloon of claim 1, wherein the polyethylene is formed of particles having a size of about 0.1 $\mu$m to about 40 $\mu$m.

7. The balloon of claim 1, wherein the polyethylene has a porosity of about 20% to about 90%.

8. The balloon of claim 1, wherein the polyethylene exhibits volumetric compressibility in the uninflated state.

9. The balloon of claim 1, wherein the balloon expands compliantly at pressures below about 8 atm and substantially less compliantly at pressures above about 8 atm.

10. The balloon of claim 9, wherein the balloon has an outer diameter which expands by about 100% to about 400% of the uninflated diameter at pressures below about 8 atm.

11. The balloon of claim 1, wherein the balloon further comprises an elastomeric layer.

12. The balloon of claim 11, wherein the elastomeric layer is an inner layer of the balloon.

13. The balloon of claim 1 wherein the ultrahigh molecular weight polyethylene has a negative Poisson ratio.

14. The balloon of claim 1 wherein the ultrahigh molecular weight polyethylene exhibits microstructural rearrangement during inflation of the balloon.

15. The balloon of claim 1 wherein the microstructural rearrangement occurs at balloon inflation pressures above 8 atm.

16. A balloon for an intraluminal catheter, wherein the balloon comprises ultrahigh molecular weight polyolefin.

* * * * *